(12) United States Patent
Guitelman

(10) Patent No.: US 9,770,273 B2
(45) Date of Patent: Sep. 26, 2017

(54) DISPOSABLE INTRAMEDULLARY DEVICE FOR TEMPORARY USE FOR TREATMENT OF LIMB INFECTIONS

(71) Applicant: Laboratorios S.L. S.A., San Fernando, Buenos Aires (AR)

(72) Inventor: Gustavo Guitelman, Buenos Aires (AR)

(73) Assignee: LABORATORIOS S.L. S.A., Buenos Aires (AR)

( * ) Notice: Subject to any disclaimer, the term of this patent is extended or adjusted under 35 U.S.C. 154(b) by 872 days.

(21) Appl. No.: 13/677,972

(22) Filed: Nov. 15, 2012

(65) Prior Publication Data

US 2013/0172827 A1 Jul. 4, 2013

(30) Foreign Application Priority Data

Nov. 16, 2011 (AR) .................. P110104271

(51) Int. Cl.
| | | |
|---|---|---|
| A61B 17/72 | (2006.01) |
| A61L 31/10 | (2006.01) |
| A61L 31/14 | (2006.01) |
| A61L 31/16 | (2006.01) |
| A61B 17/56 | (2006.01) |
| A61B 17/00 | (2006.01) |
| A61M 37/00 | (2006.01) |

(52) U.S. Cl.
CPC .............. *A61B 17/72* (2013.01); *A61L 31/10* (2013.01); *A61L 31/14* (2013.01); *A61L 31/16* (2013.01); *A61M 37/00* (2013.01); *A61B 17/7283* (2013.01); *A61B 2017/00004* (2013.01); *A61B 2017/561* (2013.01); *A61L 2300/406* (2013.01)

(58) Field of Classification Search
CPC .......... A61M 25/0012; A61M 25/0015; A61M 25/003; A61M 25/0045; A61M 25/005
See application file for complete search history.

(56) References Cited

U.S. PATENT DOCUMENTS

| | | | |
|---|---|---|---|
| 4,863,444 A | 9/1989 | Blömer | |
| 4,875,475 A | 10/1989 | Comte et al. | |
| 6,228,086 B1 | 5/2001 | Wahl et al. | |
| 6,663,634 B2 * | 12/2003 | Ahrens | A61B 17/866 606/309 |

(Continued)

FOREIGN PATENT DOCUMENTS

| | | |
|---|---|---|
| DE | 3533369 A1 | 3/1987 |
| WO | 01/39812 A1 | 6/2001 |
| WO | 2006/090226 A1 | 8/2006 |

*Primary Examiner* — Emily Schmidt
*Assistant Examiner* — Lauren M Peng
(74) *Attorney, Agent, or Firm* — Volpe and Koenig, P.C.

(57) ABSTRACT

A disposable intramedullary device for temporary use for treatment of limb infections comprising a solid core of variable cross-section, including a distal portion, a middle portion and a proximal portion, said proximal portion and distal portion including anchoring regions consisting of through-holes being passed through by bone anchoring means. Outside said anchoring regions, said solid core is coated with a polymer layer which also includes antibiotic, the outer diameter of the solid core and polymer layer assembly being equivalent to that of an intramedullary channel, and the outer diameter of said solid core in said anchoring regions being equivalent to that of said intramedullary channel.

6 Claims, 1 Drawing Sheet

(56) References Cited

U.S. PATENT DOCUMENTS

| | | |
|---|---|---|
| 6,808,527 B2 | 10/2004 | Lower et al. |
| 2002/0103488 A1* | 8/2002 | Lower .................... A61B 17/72 606/62 |
| 2003/0208166 A1* | 11/2003 | Schwartz ...................... 604/266 |
| 2008/0262630 A1 | 10/2008 | Fulmer et al. |
| 2009/0043307 A1* | 2/2009 | Faccioli ................. A61B 17/72 606/62 |
| 2010/0094347 A1* | 4/2010 | Nelson ............... A61B 17/1717 606/254 |
| 2011/0208189 A1 | 8/2011 | Faccioli et al. |
| 2012/0208753 A1* | 8/2012 | Diwan et al. .................. 514/8.8 |

* cited by examiner

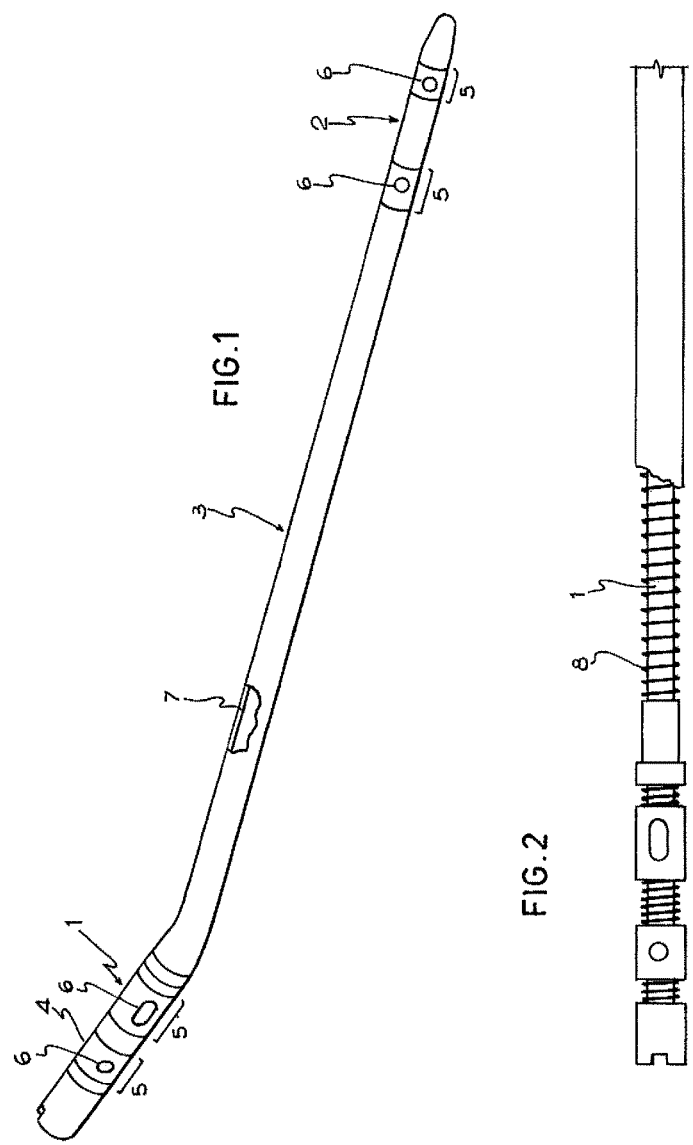

DISPOSABLE INTRAMEDULLARY DEVICE FOR TEMPORARY USE FOR TREATMENT OF LIMB INFECTIONS

CROSS REFERENCE TO RELATED APPLICATIONS

This application is a U.S. patent application which claims priority of Argentine Patent application AR P110104271, filed Nov. 16, 2011, which is incorporated by reference as if fully set forth The present invention relates to a disposable intramedullary device for temporary use for treatment of limb infections, particularly limbs having long bones susceptible to stabilization through an intramedullary nail.

A great variety of intramedullary nails are known for treatment of limb fractures, specifically arms and legs. In particular, as a way of example, documents U.S. Pat. No. 6,808,527, U.S. Pat. No. 6,228,086, and U.S. Pat. No. 4,875,475 can be mentioned. The intramedullary nails disclosed by these documents comprise proximal, middle and distal portions. The proximal portion generally includes a longitudinal groove adapted to receive at least one fixation element, the distal portion having at least one cross-sectional hole. Screws are then used for fixation said nails to the fractured bone (or fractured bones) forming said limb. These intramedullary nails are generally hollow, made of a high-strength metal material, and frequently they are not prepared to cope with an eventual infection in the implantation zone.

To this end, and to solve the infection problem caused in the surroundings of the previously mentioned devices, publication WO2006/090226 A1 discloses a disposable intramedullary device for treatment of infections in limbs that have experienced some kind of fracture. This device consists of an intramedullary nail covered by a tubular member made of a relatively rigid and biologically compatible base material, and having pores for impregnation with drugs or medicaments for treatment of infections, prior to or during insertion thereof in the stabilization site. This tubular member acts as a "cover" because the intramedullary nail inserts within said tubular member during a surgical procedure, thus creating a ready-to-use device, the manufacture thereof by skilled personnel being unnecessary. It enhances the use of materials, discarding waste materials, and reduces the time required for fitting said "cover" onto said nail. This tubular member includes means for anchoring the same to the intramedullary nail, generally an adhesive material. Again, the intramedullary device employed is generally hollow, and made of a high-strength metal material. Once the infection has healed, said device is replaced by the permanent intramedullary nail.

On the other hand, the article by Raghuram Thonse and Janet D. Conway, Journal of Bone and Joint Surgery 2008; 90:163-174, discloses intramedullary nails coated with antibiotic cement for treatment of segmented bones, wherein the whole preparation process of said nails in the surgical setting may be observed. This technique implies dead time at the operating room, and it does not ensure homogeneity in the mixture or thickness of the polymer-antibiotic layer.

Furthermore, the disadvantage of the "cover" disclosed by document WO2006/090226 A1 is that it may slide or deteriorate during insertion of the nail into the bone to be treated, due to insufficient adhesion thereof to the nail resulting from a low quality adhesive material, or because of lack of expertise from the personnel in charge of "covering" said nail. There is also the risk that the means of anchoring to the bone, commonly fastening screws so-called "locking screws", during assembly of the device, may damage the "cover". An intramedullary channel has a diameter that varies according to the kind of bone and the patient to be treated. For example, a femoral intramedullary channel ranges between 9 and 15 mm, a tibial intramedullary channel ranges between 8 and 13 mm. The nail of the above-mentioned application, together with the cover enclosing thereof reaches said diameters; however, as the "cover" encloses the whole length of said metal core, in the anchoring regions, the nail has reduced resistance to torsional and bending stresses. The device of the invention has a solid core which outer diameter in the anchoring region is equivalent to that of the intramedullary channel where it inserts into, said solid core emerging in a clean way, i.e. without any polymer and antibiotic layer covering it. Besides, the outer diameter of the metal core of the device of the invention is slightly smaller in those regions other than the anchoring regions, wherein it is indeed covered by said polymer and antibiotic layer, being of circular section, thus providing deformation without losing shear resistance, and preventing the polymer and antibiotic layer from sliding due to axial displacement, as it could be the case with a "cover", such as previously mentioned.

As a result, the device of the invention overcomes said shortcomings in view of the novel combination of a variable section solid core, coated with a layer consisting of a polymer and an antibiotic, which is arranged between the proximal and distal ends of said nail such that its displacement is impossible, while also maintaining the intramedullary space of the bone. The anchoring region cleanly emerges over said polymer and antibiotic layer taking the same outer diameter so as not to weaken the zone that is prone to the highest stresses, thus also ensuring advance of the anchoring means to the bone at minor risk of material dragging, and preventing—at the time of linking the "locking screws"—contact thereof with the edge of the hole and damage of the polymer and antibiotic layer, as it is the case of the "cover" of the above-mentioned PCT application. Besides, the device of the invention is disposable, and its use is temporary. In addition, the advantages of the device of the invention over those manufactured in situ, i.e. at the operating room, include: homogeneous distribution of the antibiotic, uniform thickness, and reduced time in the operating room for the patient, thus minimizing costs and risks for the patient under surgery.

Therefore, it is an object of the present application to provide a disposable intramedullary device for temporary use for treatment of limb infections, said device comprising a solid core of variable cross-section, including a distal portion, a middle portion, and a proximal portion, among which the distal portion and the proximal portion include anchoring regions consisting of through-holes being passed through by bone anchoring means, wherein outside said anchoring regions, said solid core is coated with a layer of polymer including antibiotic, the outer diameter of the solid core and polymer layer assembly being equivalent to that of an intramedullary channel, and in that the outer diameter of said solid core in said anchoring regions is equivalent to that of said intramedullary channel.

BRIEF DESCRIPTION OF THE DRAWINGS

For the sake of clarity, the invention will now be described in more detail with reference to the following figures that are included as a way of example and in accordance with preferred embodiments, namely:

FIG. 1 is a perspective view of the intramedullary device of the present invention.

FIG. 2 is an embodiment of the intramedullary device of the present invention.

DETAILED DESCRIPTION OF THE INVENTION

FIG. 1 is a perspective view of the device of the present invention. Said Figure illustrates a solid core 1, preferably metallic, of variable cross-section, having a distal portion 2, a middle portion 3, and a proximal portion 4. Anchoring regions 5 consisting of through-holes 6 are observed in both proximal portion 2 and distal portion 4, said through-holes being passed through by bone anchoring means, more specifically anchoring screws (not illustrated). Outside said anchoring regions 5, said solid core 1 is coated with a polymer layer 7 which also includes an antibiotic. Said layer is obtained through a specific die, and the mixture of polymer and antibiotic drains in those regions of the solid core other than the anchoring regions 5. The preferred thickness of said polymer and antibiotic layer is up to 3 mm.

On the other hand, in said anchoring regions 5, only the outer diameter of said solid core 1 is equivalent to the diameter of an intramedullary channel, since there is no such polymer and antibiotic layer 7 coating the same. This offers two advantages:

1) it ensures that the regions coated with said polymer and antibiotic layer will not slide axially (as it may occur with a cover); and
2) it ensures maximum resistance to tensile and torsional mechanical stresses (shear stresses) in the anchoring regions.

Subsequently, outside said anchoring regions 5, wherein said solid core 1 is indeed coated with said polymer and antibiotic layer 7, the outer diameter of said solid core 1 is slightly smaller, and of circular section, the outer diameter of the core 1 and layer 7 assembly being equivalent to that of the intramedullary channel. The section of said solid core 1, wherein it is covered with said polymer and antibiotic layer 7, is circular (generally, it is an annular section), allowing the device of the invention to keep its deformation without losing its shearing strength.

FIG. 2 illustrates a particular embodiment of the intramedullary device 1 of the present invention. In particular, the solid core 1 is surrounded, preferably helically surrounded, by a solid element, e.g. a wire, of small section that is preferably circular and/or polygonal, to contribute to the integrity of the polymer and antibiotic layer 7 disposed thereon. This ensures that, in case of impact, the polymer and antibiotic layer 7 may smash, but it will remain joined to the solid element helically arranged given its particular geometry.

The invention claimed is:

1. A disposable intramedullary device for temporary use for treatment of limb infections comprising a solid core of variable cross-section, including a distal portion, a middle portion and a proximal portion, the proximal portion and the distal portion comprising anchoring regions comprising through-holes for being passed through by anchoring screws, wherein
   the solid core is coated with a polymer layer including antibiotic outside the anchoring regions and is not coated with the polymer layer including antibiotic in the anchoring regions,
   the outer diameter of the device is equivalent to that of an intramedullary channel,
   the diameter of the solid core in the anchoring regions equals the outer diameter of the device, and
   the diameter of the solid core outside the anchoring regions is smaller than the diameter of the solid core in the anchoring regions such that the outer diameter of the device outside of the anchoring regions remains equivalent to the diameter of the intramedullary channel.

2. The device according to claim 1, wherein the polymer layer including antibiotic has a thickness up to 3 mm.

3. The device according to claim 1, wherein outside the anchoring regions, the cross-section of the solid core is circular.

4. The device according to claim 1, wherein the solid core is helically surrounded by a solid element of small section to contribute to the integrity of the polymer layer including antibiotic arranged thereon.

5. The device according to claim 4, wherein the section of the solid element is one or more of circular or polygonal.

6. The device according to claim 4, wherein the solid element is a wire.

* * * * *